US008022159B2

(12) United States Patent
Rachita et al.

(10) Patent No.: US 8,022,159 B2
(45) Date of Patent: Sep. 20, 2011

(54) TERMINATING COMPOUNDS, POLYMERS, AND THEIR USES IN RUBBER COMPOSITIONS AND TIRES

(75) Inventors: Michael Joseph Rachita, North Canton, OH (US); Joseph John Kulig, Tallmadge, OH (US); Robert Alan Woloszynek, Brunswick, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 79 days.

(21) Appl. No.: 12/276,454

(22) Filed: Nov. 24, 2008

(65) Prior Publication Data

US 2010/0130664 A1 May 27, 2010

(51) Int. Cl.
C08F 236/10 (2006.01)
(52) U.S. Cl. ........................................ 526/340; 526/347
(58) Field of Classification Search .................. 526/347, 526/340
See application file for complete search history.

(56) References Cited

U.S. PATENT DOCUMENTS

| | | | |
|---|---|---|---|
| 2,881,184 | A | 4/1959 | Pike |
| 3,346,588 | A | 10/1967 | Ashby |
| 4,483,973 | A | 11/1984 | Lucas et al. |
| 4,597,801 | A | 7/1986 | Stratta et al. |
| 4,672,003 | A | 6/1987 | Letoffe |
| 4,918,140 | A | 4/1990 | Peccoux et al. |
| 4,988,755 | A | 1/1991 | Dickens, Jr. et al. |
| 5,420,196 | A | 5/1995 | Lucas |
| 5,652,310 | A | 7/1997 | Hsu et al. |
| 5,811,479 | A | 9/1998 | Labauze |
| 5,821,290 | A | 10/1998 | Labauze |
| 5,916,961 | A | 6/1999 | Hergenrother et al. |
| 6,008,295 | A | 12/1999 | Takeichi et al. |
| 6,121,354 | A | 9/2000 | Chronister |
| 6,228,908 | B1 | 5/2001 | Takeichi et al. |
| 6,255,404 | B1 | 7/2001 | Hogan et al. |
| 6,767,551 | B2 | 7/2004 | McGhee et al. |
| 6,867,265 | B2 | 3/2005 | Halasa et al. |
| 6,949,294 | B2 | 9/2005 | Kashiwagi et al. |
| 7,066,228 | B2 | 6/2006 | Grimberg et al. |
| 7,202,306 | B2 | 4/2007 | Tanaka et al. |
| 7,238,740 | B2 | 7/2007 | Belin et al. |
| 7,241,823 | B2 | 7/2007 | Kashiwagi et al. |
| 7,288,594 | B2 | 10/2007 | Ozawa et al. |
| 2004/0209972 | A1 | 10/2004 | Chambers et al. |
| 2005/0070672 | A1 | 3/2005 | Ozawa et al. |
| 2005/0159554 | A1 | 7/2005 | Endou et al. |
| 2006/0272760 | A1 | 12/2006 | Teratani et al. |
| 2007/0123640 | A1 | 5/2007 | Cross et al. |

FOREIGN PATENT DOCUMENTS

| | | |
|---|---|---|
| DE | 3414877 A1 | 10/1985 |
| EP | 0 176 983 A2 | 9/1986 |
| EP | 0 206 301 A1 | 12/1986 |
| EP | 0 313 482 A1 | 4/1989 |
| EP | 0 767 206 A1 | 4/1997 |
| EP | 0 780 421 A2 | 6/1997 |
| EP | 0 786 493 A1 | 7/1997 |
| EP | 1 479 698 A1 | 11/2004 |
| EP | 1925636 A | 3/2007 |
| EP | 1854838 A | 11/2007 |
| EP | 1854839 A | 11/2007 |
| EP | 1860146 A | 11/2007 |
| EP | 1 925 636 * | 5/2008 |
| FR | 2572415 | 5/1986 |
| GB | 2137217 | 10/1984 |
| JP | 59 12964 | 1/1984 |
| JP | 2 153963 | 6/1990 |
| JP | 9 136893 | 5/1997 |
| JP | 11349632 A | 12/1999 |
| JP | 2001131230 | 5/2001 |
| JP | 2001158834 | 6/2001 |
| JP | 2001158835 | 6/2001 |
| JP | 2001158836 | 6/2001 |
| JP | 2001158837 | 6/2001 |
| JP | 2002114012 | 4/2002 |
| JP | 2002302593 A | 10/2002 |
| JP | 2003155381 | 5/2003 |
| JP | 2003238808 | 8/2003 |
| JP | 2004269818 | 9/2004 |
| JP | 2004269819 | 9/2004 |
| JP | 2005232351 | 9/2005 |
| JP | 2005232367 | 9/2005 |
| JP | 2005336347 | 12/2005 |
| JP | 2006152211 | 6/2006 |
| JP | 2006183036 | 7/2006 |
| JP | 2007284569 | 11/2007 |
| JP | 2008038119 | 2/2008 |
| WO | 01 34659 A1 | 5/2001 |
| WO | 02 02356 A1 | 1/2002 |
| WO | 0210265 A1 | 2/2002 |
| WO | 02 22728 A1 | 3/2002 |
| WO | 03/044026 A1 | 5/2003 |
| WO | 03 046020 A1 | 6/2003 |
| WO | 03 048216 A1 | 6/2003 |
| WO | 03 087171 A1 | 10/2003 |
| WO | 2006093051 A1 | 9/2006 |
| WO | 2006112450 A1 | 10/2006 |
| WO | 2007032209 A1 | 3/2007 |
| WO | 2007034785 A1 | 3/2007 |

(Continued)

OTHER PUBLICATIONS

European Patent Office, International Search Report and Written Opinion, dated May 28, 2009, 4 pages.

(Continued)

*Primary Examiner* — Kuo-Liang Peng
(74) *Attorney, Agent, or Firm* — Wood, Herron & Evans, LLP

(57) ABSTRACT

The invention includes terminating compounds, polymers, rubber compositions and tires. The terminating compounds can provide terminating groups on the polymer. Polymers can be homopolymers, copolymers and terpolymers, and can include repeat units provided from conjugated diene monomers. Rubber compositions can be made from the polymers, and tires and various parts of tires can be made from those rubber compositions.

15 Claims, No Drawings

FOREIGN PATENT DOCUMENTS

| | | |
|---|---|---|
| WO | 2008004675 A1 | 1/2008 |
| WO | 2008004676 A1 | 1/2008 |
| WO | 2008013090 A1 | 1/2008 |

OTHER PUBLICATIONS

U.S. Patent and Trademark Office, Non-Final Office Action received in related U.S. Appl. No. 12/030,224 dated Apr. 14, 2010, 22 pages.
EP 313482—English Language Abstract only, obtained from http://ep.espacenet.com/, 1989.
EP 767206—English Language Abstract only, obtained from http://ep.espacenet.com/, 1997.
EP 786493—English Language Abstract only, obtained from http://ep.espacenet.com/, 1997.
JP 2153963—English Language Abstract only, obtained from http://ep.espacenet.com/, 1990.
JP 9136893—English Language Abstract only, obtained from http://ep.espacenet.com/, 1997.
JP 59012964—English Language Abstract only for JP59-12964, obtained from http://ep.espacenet.com/, 1984.
JP 2001131230—English Language Abstract only, obtained from http://ep.espacenet.com/, 2001.
JP 2001158837—English Language Abstract only, obtained from http://ep.espacenet.com/, 2001.
JP 2001158834—English Language Abstract only, obtained from http://ep.espacenet.com/, 2001.
JP 2001158835—English Language Abstract only, obtained from http://ep.espacenet.com/, 2001.
JP 2001158836—English Language Abstract only, obtained from http://ep.espacenet.com/, 2001.
JP 2002114012—English Language Abstract only, obtained from http://ep.espacenet.com/, 2002.
JP 2003155381—English Language Abstract only, obtained from http://ep.espacenet.com, 2003.
JP 2003238808—English Language Abstract only, obtained from http://ep.espacenet.com/, 2003.
JP 2004269818—English Language Abstract only, obtained from http://ep.espacenet.com/, 2004.
JP 2004269819—English Language Abstract only, obtained from http://ep.espacenet.com/, 2004.
JP 2005232351—English Language Abstract only, obtained from http://ep.espacenet.com/, 2005.
JP 2005232367—English Language Abstract only, obtained from http://ep.espacenet.com/, 2005.
JP 2005336347—English Language Abstract only, obtained from http://ep.espacenet.com/, 2005.
JP 2006183036—English Language Abstract only, obtained from http://ep.espacenet.com/, 2006.
JP 2007284569—English Language Abstract only, obtained from http://ep.espacenet.com/, 2007.
JP 2008038119—English Language Abstract only, obtained from http://ep.espacenet.com/, 2008.
JP2006152211—English Language Abstract only, obtained from http://ep.espacenet.com/, 2006.
FR 2572415—English Language Abstract only, obtained from http://ep.espacenet.com/, 1987.
Alder et al., Chem. Commun., vol. 1, pp. 131-132, 1998.
Mueller et al., Polymeric Materials Science and Engineering, vol. 76, pp. 51-52, 1997.
Extended European Search Report and Opinion issued in counterpart European Application No. 09175907.6, mailed on Sep. 14, 2010 (7 pgs.).

* cited by examiner

TERMINATING COMPOUNDS, POLYMERS, AND THEIR USES IN RUBBER COMPOSITIONS AND TIRES

BACKGROUND

It is sometimes desirable for tires to have a combination of good wet skid resistance, low rolling resistance, tear strength, and good wear characteristics. Wear characteristics of a tire tread can be difficult to improve without sacrificing traction and/or rolling resistance. Sometimes, such properties depend upon dynamic viscoelastic properties of the tire tread rubber composition and the elastomers (rubbers) utilized in the rubber composition.

In order to reduce the rolling resistance and to improve the tread wear characteristics of tires, rubbers or rubbery polymers having a high rebound physical property (low hysteresis) have been used for the tire tread rubber compositions. However, in order to increase the wet skid resistance of a tire tread, rubbery polymers that have a relatively lower rebound physical property (higher hysteresis) which thereby undergo a greater energy loss, have sometimes been used for such tread rubber compositions. To achieve such relatively inconsistent viscoelastic properties for the tire tread rubber compositions, blends (mixtures) of various types of synthetic and natural rubber can be utilized in tire treads.

It can be desirable for synthetic rubber polymers to exhibit relatively low levels of hysteresis (indicated by relatively higher rebound values). This can be important when elastomers are used in tire tread rubber compositions. In practice, the elastomers can be conventionally blended with sulfur curative, rubber reinforcing fillers such as, for example precipitated silica and rubber reinforcing carbon black, sulfur vulcanization accelerators, rubber antidegradants and other desired rubber chemicals and are then subsequently vulcanized, or cured, under pressure at an elevated temperature in a suitable mold. The physical properties of such cured rubber compositions can depend upon the degree to which the rubber reinforcing fillers, such as carbon black or silica, are homogeneously dispersed throughout the elastomer. In some instances, the degree of homogeneity of the dispersement of the reinforcing filler relates, at least in part, to the degree of affinity that carbon black or silica have for the rubbery polymer.

Amorphous silica reinforcement has sometimes been used in combination with rubber reinforcing carbon black to promote lower rolling resistance (e.g. better vehicular fuel economy) and to promote better traction (e.g. skid and braking resistance) for a tire tread rubber composition. However, use of such silica reinforcement filler, as compared to rubber reinforcing carbon black, can result in a decrease in wear resistance (e.g. increase in tread wear) of a tire tread rubber composition.

Thus, it can be desirable to provide terminating compounds, polymers, rubber compositions, and tires made therefrom to overcome the above-described issues, as well as others.

SUMMARY

Some embodiments of the present invention relate to a terminating compound

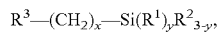

$R^3$ is

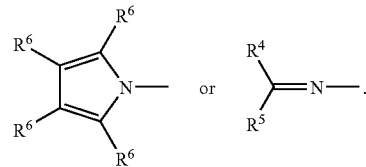

$R^1$ can be the same or different and can be an alkyl, a cycloalkyl, an allyl, and an aryl group with from about 1 to about 18 carbon atoms selected from. $R^2$ can be the same or different and can be $-O(CH_2)_pCH_3$ or $-(A(CH_2)_n)_mACH_3$ where p is 0, 1, 2, or about 3, A is S or O, n is 1, 2, or about 3, and m is 1, 2, or about 3. x can be an integer from about 1 to about 20. y can be 0, 1, or 2. $R^4$ can be an aryl or substituted aryl having from about 6 to about 18 carbon atoms, or a heterocycle or substituted heterocycle having from about 3 to about 18 carbon atoms. $R^5$ can be a hydrogen or a alkyl group having from about 1 to about 4 carbons. $R^6$ can be the same or different and can be hydrogen or an alkyl having from about 1 to about 4 carbons. If (i) $R^5$ is H and (ii) $R^4$ is a phenyl or substituted phenyl, then $R^2$ is $-(A(CH_2)_n)_mACH_3$ and m is 2 or about 3.

Still other embodiments include a polymer comprising (a) a repeat unit provided from a conjugated diene monomer and (b) a terminating group provided from the terminating compound.

Processes for making the polymer are also provided. They include, for example, polymerizing monomers comprising conjugated diene monomers by using an initiator to form a polymer with an active terminal end; followed by reacting an active terminal end of the polymer with the terminating compound.

Other embodiments include rubber compositions comprising the terminated polymer and a filler. Tires and tire components can be made from these rubber compositions.

DETAILED DESCRIPTION

The present invention relates to terminating compounds, polymers and rubber compositions, and tires made therefrom. In some embodiments, the present invention relates to a polymer that is terminated with at least one terminating group.

The terminating compounds that can provide the terminating groups on the polymer, can include those selected from the terminating compounds of Formula (I):

$R^3$ is

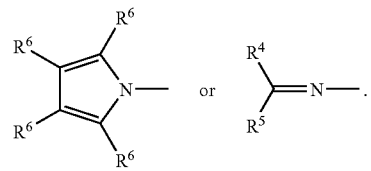

$R^1$ can be the same or different and can be an alkyl, a cycloalkyl, an allyl, or an aryl having from about 1 to about 18 carbon atoms selected from; $R^2$ can be the same or different and can be is $-O(CH_2)_pCH_3$ or $-(A(CH_2)_n)_mACH_3$ where p is 0, 1, 2, or about 3, A is S or O, n is 1, 2, or about 3, and m is 1, 2, or about 3 (e.g., $R^2$ can be —OCH$_2$CH$_2$OCH$_2$CH$_2$OCH$_3$ or glyme); x is an integer from about 1 to about 20 (e.g., 1, 2, 3, 4, or about 5); y is 0, 1, 2, or 3; $R^4$ is an aryl or substituted aryl having from about 6 to about 18 carbon atoms, or a heterocycle or substituted heterocycle having from about 3 to about 18 carbon atoms (e.g., $R^4$ can be a phenyl group); $R^5$ is a hydrogen or a alkyl group having from about 1 to about 4 carbons; $R^6$ can be the same or different and can be hydrogen or an alkyl having from about 1 to about 4 carbons (e.g., $R^3$ can be a pyrrole substituted with one, two, three or four methyl groups). In some instances, if (i) $R^5$ is H and (ii) $R^4$ is a phenyl or substituted phenyl, then $R^2$ is $-(A(CH_2)_n)_m ACH_3$ and m is 2 or about 3.

As used herein, "substituted" is defined by the substitution of a hydrogen on a carbon by a univalent group including, but not limited to, halogen, hydroxy, thiol, amino, nitro, cyano, $C_1$-$C_4$ alkyl, alkylamino, carboxy, amido, vinyl, and $C_1$-$C_5$ alkoxy.

"Aryl" as used herein, is defined to include an organic radical derived from an aromatic hydrocarbon consisting of 1-3 rings and containing about 6 to about 18 carbon atoms. Aryl includes but is not limited to, phenyl and naphthyl.

"Heterocycle" as used herein, is defined to include an aromatic (e.g., heteroaryls) or non aromatic cyclic alkyl, alkenyl, or allynyl moiety, having at least one O, S, P, B, and/or N atom interrupting the carbocyclic ring structure. Non-limiting examples of aromatic heterocycles are pyridyl, furyl, pyrrolyl, thienyl, isothiazolyl, imidazolyl, benzimidazolyl, naphthyridinyl, pyridazinyl, pyrimidinyl, pyrazinyl, quinolyl, indolyl, carbazolyl, thiazolyl, 1,2,4-thiadiazolyl, furopyranyl, and benzofuranyl. Non-limiting examples of non aromatic heterocycles are tetrahydrofuranyl, tetrahydropyranyl, piperidinyl, piperidyl, piperazinyl, imidazolidinyl, morpholino, and morpholinyl.

$R^3$ can be

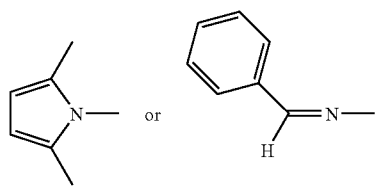

If $R^2$ is —O(CH$_2$)$_p$CH$_3$ then $R^3$ can be

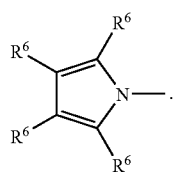

In still other embodiments, if $R^2$ is —O(CH$_2$)$_p$CH$_3$ then $R^5$ is hydrogen.

The terminating compound can be, for example, N-benzylidene-3-tris(methoxyethoxyethoxysilyl)-1-propaneamine, N-pyrrole-3-tris(methoxyethoxyethoxysilyl)-1-propaneamine, or other heteroatom containing tethered silanes such as mercapto-triglymsiloxys.

The terminating compound can be, for example,

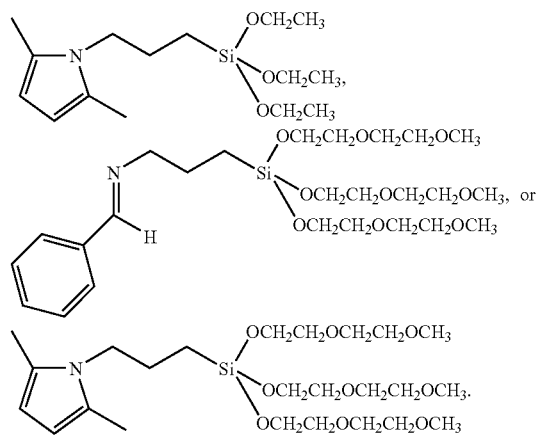

The terminating compound can be synthesized using, for example, condensation reactions between the corresponding amino silane with an aldehyde or a dialdehyde, including, for example, benzaldehyde or 2,5-hexanedione. The reaction can be performed at room temperature or at temperatures that allow for reflux. Water produced by the condensation reaction can be removed by any known method, including, for example, molecular sieves, dehydration with salts, or azeotropic distillation.

In some embodiments, $R^2$ can create a siloxy group (e.g., a bulky siloxy group) that can provide stability (e.g., from condensation) during steam stripping or that can provide reactivity to a filler during compounding (e.g., a silica filler) or both. In some instances, the liberation of $R^2$ during steam stripping or during compounding can provide a compound that reduces or prevents interference with the hexane recycle system, emission problems, or both.

When an active terminal of the polymer (e.g., a conjugated diene) is reacted with the terminating compound of Formula (I) an amine can be produced on the terminal end of the polymer. When such resultant polymer is compounded with a filler, the amine functionality can facilitate an interaction with an acidic functional group on the surface of the filler, thereby providing a filler dispersing and reinforcing effect. Further, the amine is capable of forming a hydrogen bond with a silanol group, which can cause a dispersion of silicon. Of course, other terminating agents, such as those discussed in U.S. Pat. No. 6,627,721 may additionally be used, as desired.

The terminating compound can include an $R^2$ group that can react (e.g., via a condensation reaction) with a hydroxyl group (e.g. silanol group) on the surface of the amorphous silica (e.g. precipitated silica) when introduced into an end of the resulting polymer chain. This reaction and the force of the above-mentioned hydrogen bond by the amino group can provide a reinforcing effect, and in some instances there can be synergism between the two effects.

The amount of the terminating compound used can be, for example, from about 0.25 to about 10.0 mol per one mole of initiator for polymerization (e.g., an organo-alkali metal compound). The amount of terminating compound can be, for example, from about 0.5 to about 5.0 mol per one mole of the initiator, or from about 0.75 to 1.5 mol per one mole of the initiator.

The polymer comprising the terminating compound can be a homopolymer, a copolymer or a terpolymer. Repeat units and monomers are terms used to describe the makeup of the polymer. A repeat unit differs from a monomer in that a double bond of the monomer is consumed by the polymerization reaction to provide a repeat unit that is incorporated into the polymer. Repeat units of the polymer can include those provided from conjugated diene monomers. Examples of the conjugated diene monomer include 1,3-butadiene, isoprene, 1,3-pentadiene, 2,3-dimethylbutadiene, 2-phenyl-1,3-butadiene, and 1,3-hexadiene. The conjugated diene monomer can be used to provide repeat units for a homopolymer, a copolymer, or a terpolymer. Repeat units for the copolymer or terpolymer can be provided from another conjugated diene monomer, a vinyl aromatic monomer, or a functionalized monomer, for example. Examples of the vinyl aromatic hydrocarbon monomer for use in copolymerization with the conjugated diene monomer include styrene, α-methylstyrene, 1-vinylnaphthalene, 3-vinyltoluene, ethylvinylbenzene, divinylbenzene, 4-cyclohexylstyrene, and 2,4,6-trimethylstyrene. Examples of functionalized monomers include those disclosed in U.S. Pat. No. 6,627,721, which is incorporated herein by reference in its entirety, such as 1-[(4-Ethenylphenyl)methyl]-pyrrolidine and 1-[(4-Ethenylphenyl)ethyl]-pyrrolidine.

When carrying out copolymerization using a conjugated diene monomer and a vinyl aromatic hydrocarbon monomer, the monomers, in one example, are 1,3-butadiene and styrene, respectively.

Examples of the initiator for use in the polymerization reaction include organic alkali metal compounds such as organolithium compounds. In one example, the lithium compounds have from about 2 to about 20 carbon atoms. Specific examples include ethyllithium, n-propyllithium, i-propyllithium, n-butyllithium, sec-butyllithium, t-octyllithium, n-decyllithium, phenyllithium, 2-naphthyllithium, 2-butylphenyllithium, 4-phenyl-butyllithium, cyclohexyllithium, 4-cyclopentyllithium, and a reaction product between diisopropenylbenzene and butyllithium. The amount of initiator used includes from about 0.1 to about 20 mmol based on 100 g of monomers.

The polymerization process can be carried out in a solvent, such as a hydrocarbon solvent, that does not destroy the initiator (e.g., organolithium initiators). A suitable solvent may be selected from an aliphatic hydrocarbon, an aromatic hydrocarbon, or an alicyclic hydrocarbon. In one example, the hydrocarbons have from about 3 to about 8 carbon atoms. Examples of the hydrocarbon include propane, n-butane, i-butane, n-pentane, i-pentane, n-hexane, mixed hexanes, cyclohexane, propene, 1-butene, i-butene, trans-2-butene, cis-2-butene, 1-pentene, 2-pentene, 1-hexene, 2-hexene, benzene, toluene, xylene, and ethylbenzene. These solvents may be used alone or in combination; for example, mixed hexanes, cyclohexane, and pentane can be used.

The monomer concentration in the solvent may be for example from about 5 to about 50% by weight. In another example, the concentration may be from about 10% to about 30% by weight. When carrying out copolymerization between a conjugated diene monomer and a vinyl aromatic hydrocarbon monomer, the content of the vinyl aromatic hydrocarbon monomer in the monomer mixture charged into a reactor can be for example from about 3 to about 50% by weight. In another example, the content is from about 5 to about 45% by weight.

A modifier may be used when anionic polymerization of a conjugated diene monomer is carried out. The term "modifier" is used herein to mean a compound that has a function to control the microstructure of a conjugated diene polymer and the compositional distribution of monomer units in a copolymer composed of a conjugated diene monomer and a vinyl aromatic hydrocarbon monomer. For example, the increase of the proportion of 1,2-linkage of butadiene portions of a butadiene polymer or in a butadiene portion of a butadiene-styrene copolymer, or the increase of the proportion of the 3,4-linkage of an isoprene polymer can be controlled. In addition, randomization of butadiene units or the styrene units in a butadiene-styrene copolymer, for example, can be controlled. The modifiers are not particularly limited. Examples of the modifiers include ethers such as dimethoxybenzene, tetrahydrofuran, dimethoxyethane, diethylene glycol dibutyl ether, diethylene glycol dimethyl ether, bis(tetrahydrofurylpropane), and tertiary amines such as trimethylamine, pyridine, N-methylmorpholine, N,N,N',N'-tetramethylethylenediamine, and 1,2-dipiperidinoethane. Further examples include potassium salts such as potassium-t-amylate and potassium-t-butoxide and sodium salts such as sodium-t-amylate. The amount to be used of the modifier is within the range of from about 0.01 to about 10 molar equivalents per one mole of the organolithium compound.

The reaction between the terminating compound and the polymerized (e.g., copolymerized or terpolymerized) monomer can be carried out utilizing standard temperatures for diene polymerization. Such temperatures can range from about 30° C. to about 110° C., for example. The polymerization reaction can be carried under a pressure generated by the reaction. It can be desirable to carry out the reaction under a pressure sufficient to keep the monomers substantially in a liquid phase. That is, the pressure for the polymerization reaction can depend on the substances to be polymerized, diluents to be used, and polymerization temperatures; higher pressures can be employed if desired. Such a pressure can be obtained by any appropriate method, for example, by pressurizing the reactor by a gas inert to the polymerization reaction.

It can be desirable to remove water, oxygen, carbon dioxide, and other catalyst poison from one or more of the materials, such as initiator, solvent, monomer, and the like, involved in the polymerization process.

Although the timing and method for adding the terminating compound to the polymerization system chain is not particularly limited, such a terminating compound can be added when the polymerization is completed or near completion. In some embodiments, the polymerization is carried out until high conversions of at least about 85 percent are attained. For instance, the terminating compound can be added after a monomer conversion of greater than about 85 percent has been realized.

The polymer (e.g., copolymer or terpolymer) obtained can have, for example, a glass transition point (Tg) of −95 to −10° C. as measured by DSC (Differential Scanning Calorimetry) using a heating rate of 10° C./min.

The Mooney viscosity ($ML_{1+4}/100°$ C.) of the uncured polymer may, for example, be in a range of from about 10 to about 150. In another example, the Mooney viscosity may be, for example, in a range of from about 15 to about 70.

The polymer can be exposed to steam stripping conditions in some instances to aid in recovery. For example, the polymer can be dissolved in hexane, the solution of which is exposed to steaming hot water at a pH of from about 7 to about 7.6. The exposure can be for 20, 60, or 120 minutes. In some instances this steam stripping can result in increase in the polymer molecular weight of about 30%, about 50%, about 100%, about 250%, about 270%, or about 300% or more.

The polymer can be used together with conventional rubbery polymers to provide a rubber composition for use in the tire industry. Examples of the conventional rubbery polymer include natural rubber and diene-based synthetic rubbers.

Examples of the diene-based synthetic rubbers include emulsion styrene/butadiene copolymers, solution styrene/butadiene copolymers, 1,4-cis-polybutadiene, 1,2-vinyl-polybutadiene, 1,4-cis-polyisoprene, 3,4-polyisoprene, styrene/isoprene/butadiene copolymers, isoprene/butadiene copolymers, styrene/isoprene copolymers, butyl rubber, ethylene/propylene copolymers, and blends thereof. A rubber component, having a branched structure formed by use of a polyfunctional modifier such as tin tetrachloride, or a multifunctional monomer such as divinyl benzene may also be used.

The rubber composition, which includes from about 25% to about 100% by weight polymer (with from about 50% to about 75% weight percent being one embodiment) also can include fillers. In some instances, these fillers can be rubber reinforcing fillers. The filler can be silica, carbon black, or a combination of a silica and a carbon black. Clay and/or organic fillers such as starch can also be used as fillers.

The silica can be a synthetic amorphous rubber reinforcing silica. Examples include wet-process silica (precipitated silica), dry-process silica (fumed silica), calcium silicate, and aluminum silicate. In one example, the silica is precipitated silica.

Examples of various carbon blacks may be found, for example, the Vanderbilt Rubber Handbook, 13$^{th}$ Edition (1990) pages 416 through 418.

The amount of the filler used in the rubber composition can be, for example, within a range of from about 10 to about 130 phr (e.g. in a range of from about 20 to about 110 phr).

When synthetic amorphous silica (e.g. precipitated silica) is used as filler in the rubber composition, a silica coupling agent can be used to further increase the reinforcing property at the time when the silica is incorporated. Such silica coupling agents have a moiety reactive with hydroxyl groups (e.g. silanol groups), on the silica filler and another different moiety interactive with the conjugated diene derived elastomer. Examples include organoalkoxymercapto silanes and bis(3-trialkoxysilylalkyl)polysulfides having an average of about 2 to 4 connecting sulfur atoms in its polysulfidic bridge. Examples of the silica coupling agent comprise, for example, bis(3-triethoxysilylpropyl)tetrasulfide, bis(3-triethoxysilylpropyl)disulfide, bis(2-triethoxysilylethyl)tetrasulfide, bis(3-trimethoxysilylpropyl)tetrasulfide, bis(2-trimeth-oxysilylethyl)tetrasulfide, 3-mercapto-propyltrimethoxysilane, 3-mercaptopropyl-triethoxysilane, 2-mercaptoethyltrimethoxysilane, 2-mercaptoethyltriethoxysilane, 3-nitropropyltrimethoxysilane, 3-nitropropyl-triethoxysilane, 3-chloropropyltrimethoxysilane, 3-chloropropyltriethoxysilane, 2-chloroethyltrimethoxy-silane, 2-chloroethyltriethoxysilane, 3-trimethoxysilylpropyl-N,N-dimethylthiocarbamoyl tetrasulfide, 3-triethoxysilylpropyl-N,N-dimethylthiocarbamoyl tetrasulfide, 2-triethoxy-silylethyl-N,N-dimethylthiocarbamoyl tetrasulfide, 3-trimethoxysilylpropylbenzothiazole tetrasulfide, 3-triethoxysilyl-propylbenzothiazole tetrasulfide, 3-triethoxysilylpropyl-methacylate monosulfide, 3-trimethoxysilylpropylmethacylate monosulfide, bis(3-diethoxy-methylsilylpropyl)tetrasulfide, 3-mercaptopropyldimethoxymethylsilane, 3-nitropropyl-dimethoxymethylsilane, 3-chloropropyldimethoxymethylsilane, dimethoxymethylsilylpropyl-N,N-dimethyl-thiocarbamoyl tetrasulfide, and dimethoxymethylsilylpropylbenzothiazole tetrasulfide.

The polymer can have a functional group having a high affinity for silica. Therefore, even when the content of silica coupling agent, which is expensive, in the rubber composition is lower than a conventional content, the use of the polymer can enable the rubber composition to exhibit physical properties competitive with those of conventional ones. Although the amount of silica reinforcement can vary (e.g., in some instances it can depend on the kind of the silica coupling agent), the amount of silica coupling agent can be, for example, in a range of from about 1 to about 20 weight percent based on the amount of the silica. In some embodiments, the amount of silica coupling agent can be, for example, in a range of from about 5 to about 15 weight percent based on the amount of the silica.

Examples of vulcanizing agents include sulfur and sulfur containing compounds. The amount of the vulcanizing agent to be used may be for example from about 0.1 to about 10.0 phr. For example, the amount may be from about 1.0 to about 5.0 phr.

Examples of the process oil include for example paraffin-based oils, naphthene-based oils, and aromatic-based oils. The amount to be used of the process oil may be, for example from about 0 to about 100 phr.

The vulcanization accelerators may include for example thiazole-based ones, such as 2-mercaptobenzothiazole, dibenzothiazyl disulfide, and sulphenamides such as for example N-cyclohexyl-2-benzothiazyl sulphenamide, and guanidine-based ones such as for example diphenylguanidine. The amount to be used of the vulcanization accelerator may be, for example, from about 0.1 to about 5.0 phr or from about 0.2 to about 3.0 phr.

The rubber composition of the present invention may also typically contain additives that are conventionally used in rubber industries, for example, are antioxidants, zinc oxide, stearic acid, waxes and antidegradients.

The rubber composition may be obtained by milling the ingredients using a kneading apparatus such as a roll mill, an internal mixer, and the like. After being shaped, the rubber composition can be vulcanized. The rubber composition can be used in various tire components, such as tire treads, under treads, carcasses, side walls, and beads, and in other industrial applications such as rubber cushions, belts, and hoses, for example. In one example, the rubber composition is suitable as a rubber composition for tire treads.

As described above, the polymer exhibits good reinforcing characteristics in a rubber composition having a filler which includes amorphous silica and/or rubber reinforcing carbon black.

The rubber composition can be tested for room temperature rebound, tan δ (indicative of rolling resistance), and Din abrasion (indicative of treadwear). The values of RT rebound can range, for example, from about 39 to about 50, and can include 41, 42, 43, 44, 45, 46, and 48. The values of tan δ can, for example, range from 0.10 to about 0.25 and can include 0.13, 0.15, 0.17, 0.2, and 0.23. The values of Din abrasion can, for example, range from about 80 to about 145, and can include 90, 100, 110, 115, 120, 125, 130, 135, and 140.

In order to further illustrate the present invention, the following specific examples are given. It should be understood that the examples are not limitations of the scope of the present invention. In the examples, phr means parts per hundred parts rubber (i.e., the inventive polymer plus any additional polymer) by weight and % values are by weight unless otherwise specified.

EXAMPLES

Synthesis of Terminating Compounds

Example 1

Synthesis of
N-benzylidene-3-(triethoxysilyl)-1-propaneamine:

(Imine-TEOS) To a 2000 mL 3-neck round bottom flask placed in an ice water bath and equipped with a stirbar was added 70 g of 5 Å molecular sieves. The flask was then equipped with a reflux condenser and the remaining necks were sealed with rubber septa. The reaction flask was evacuated and backfilled with dry nitrogen three times. After the final backfill cycle, 200.1 g (903.9 mmol) of 3-aminopropyltriethoxysilane was added to the flask, along with 300 mL of anhydrous toluene. With rapid stirring, 95.9 g (903.9 mmol) of benzaldehyde was added dropwise via cannula over 30 minutes. The contents were allowed to stir at room temperature under nitrogen overnight. After an overnight stir, the contents were filtered. An additional 50 mL of anhydrous toluene was added to facilitate the filtration. The filtrate was filtered a second time and collected. The collected filtrate was concentrated via rotary evaporation to yield a pale gold oil (274.9 g, 98%). This solid was isolated in >98% purity, as characterized by $^1$H NMR spectroscopy and was not purified further. $^1$H NMR (CDCl$_3$, 400 MHz): 0.68 (m, 2H); 1.22 (m, 9H); 1.85 (m, 2H); 3.61 (m, 2H); 2.82 (m, 6H); 7.40 (m, 3H); 7.72 (m, 2H); 8.27 (s, 1H).

Example 2

Synthesis of N-benzylidene-3-tris(methoxyethoxyethoxysilyl)-1-propaneamine:

(Imine-GLYME) To a 1000 mL 3-neck round bottom flask equipped with a stirbar was added 20 g (5× the amount of water generated by the reaction by weight) of 5 Å molecular sieves. The flask was then equipped with a reflux condenser and the remaining necks were sealed with rubber septa. The reaction flask was evacuated and backfilled with dry nitrogen three times. After the final backfill cycle, 97.4 g (220 mmol) of 3-aminopropyltris(methoxyethoxyethoxy)silane was added to the flask, along with 300 mL of anhydrous toluene. With rapid stirring, 23.3 mL (231 mmol) of benzaldehyde was added dropwise via cannula over 30 minutes. The contents were heated to reflux and stirred under nitrogen overnight. After an overnight stir, the contents were filtered. An additional 50 mL of anhydrous toluene was added to facilitate the filtration. The filtrate was filtered a second time and collected. The collected filtrate was concentrated via rotary evaporation to yield a pale gold oil (115.4 g, 99%). This solid was isolated in >98% purity, as characterized by $^1$H NMR spectroscopy and was not purified further. $^1$H NMR (CDCl$_3$, 400 MHz): 0.75 (m, 2H); 1.85 (m, 2H); 3.69 (m, 2H); 3.25-3.90 (m, 33H); 7.38 (m, 3H); 7.65 (m, 2H); 8.25 (s, 1H).

Example 3

Synthesis of Pyrrole-3-(triethoxysilyl)-1-propaneamine:

(Pyrrole-TEOS) To a 500 mL 3-neck round bottom flask equipped with a stirbar was added 30.8 g (10× the amount of water generated by the reaction by weight) of 5 Å molecular sieves. The flask was then equipped with a reflux condenser and the remaining necks were sealed with rubber septa. The reaction flask was evacuated and backfilled with dry nitrogen three times. After the final backfill cycle, 18.9 g (85.4 mmol) of 3-aminopropyltriethoxysilane was added to the flask, along with 40 mL of anhydrous toluene. With rapid stirring, 10.8 mL (89.7 mmol) of 2,5-hexanedione was added dropwise via syringe. The contents were heated to reflux and stirred under nitrogen overnight. After an overnight stir, the contents were filtered. The filtrate was filtered a second time and collected. The collected filtrate was concentrated via rotary evaporation to yield an orange liquid (23.7 g, 94%). This solid was isolated in >98% purity, as characterized by $^1$H NMR spectroscopy and was not purified further. $^1$H NMR (CDCl$_3$, 400 MHz): 0.65 (m, 2H); 1.23 (m, 9H); 1.75 (m, 2H); 2.23 (s, 6H) 3.77 (m, 2H); 3.84 (m, 6H); 5.76 (s, 2H). $^{13}$C NMR (CDCl$_3$, 100 MHz): 7.64; 12.43; 18.26; 24.38; 45.99; 58.42; 104.91; 127.28.

Example 4

Synthesis of Pyrrole-3-tris(methoxyethoxyethoxysilyl)-1-propaneamine:

(Pyrrole-GLYME) To a 100 mL round bottom flask equipped with a stirbar was added 4.36 g (10× the amount of water generated by the reaction by weight) of 5 Å molecular sieves. The flask was then equipped with a reflux condenser and sealed with rubber septa. The reaction flask was evacuated and backfilled with dry nitrogen three times. After the final backfill cycle, 5.35 g (12.1 mmol) of 3-aminopropyltris(methoxyethoxyethoxy)silane was added to the flask, along with 25 mL of anhydrous toluene. With rapid stirring, 1.43 mL (12.2 mmol) of 2,5-hexanedione was added dropwise via syringe over one minute. The contents were heated to reflux and stirred under nitrogen overnight. After an overnight stir, the contents were filtered. The filtrate was filtered a second time and collected. The collected filtrate was concentrated via rotary evaporation to yield an orange viscous oil (5.94 g, 94%). This solid was isolated in >98% purity, as characterized by $^1$H NMR spectroscopy and was not purified further. $^1$H NMR (CDCl$_3$, 400 MHz): 0.4-0.75 (m, 2H); 1.5-1.9 (m, 2H); 2.15 (br.s, 6H) 3.9 (m, 2H); 3.30-3.75 (m, 33H); 5.75 (s, 2H).

Preparation of Polymers

Example 5

Preparation of control polymer:

Polymerizations were carried out in a one gallon batch reactor under moderate stirring and inert nitrogen atmosphere. The reactor is equipped with a variable speed agitator and a heating/cooling jacket to control the reactor temperature via a distributed Foxboro control system. Prior to polymer loading, the reactor was filled with dry hexane and quenched with n-BuLi to minimize the scavenger level. The reaction temperature was set at 60° C. Approximately 1500 grams of 14.5 wt % premix (25/75 wt/wt styrene/butadiene in hexane) was charged into the reactor after it was first passed through a bed of molecular sieves and silica gel under a nitrogen atmosphere. N-Butyl-lithium initiator and N,N,N', N'-tetramethylethylenediamine (TMEDA) modifier were introduced via common syringe techniques. Conversion data was determined gravimetrically or by gas chromatography (GC) analysis of residual monomer. For GC testing, aliquots of the reaction mixture were taken via the dip leg during the course of polymerization and collected into a 60/40 (w/w) solution of ethanol/decane. Polymerizations were terminated after full conversion was reached by treating the live polymer cement with an isopropanol/BHT antioxidant solution. The polymer was recovered by drum drying. The target polymer Mooney viscosity (ML$_{(1+4)}$/100° C.) was 40 with a Tg (glass transition temperature) of approximately −25° C.

Example 6

Preparation of polymers terminated with terminating compounds:

Polymers were prepared as described in Example 5 with the exception that isopropanol/BHT termination was replaced with the appropriate terminating compound, as discussed further below, used at one molar equivalent to the amount of butyl-lithium used to initiate the polymerization. Base Mooney viscosity ($ML_{(1+4)}/100°$ C.) prior to the termination was approximately 40 for all functional polymers and Tg of $-25°$ C.

Polymers (a)-(e) were prepared as described in Example 5 and Example 6 using terminating agent (a) and terminating compounds (b)-(e), respectively, as shown below:

(a) Control—isopropanol

(b) N-benzylidene-3-(triethoxysilyl)-1-propaneamine

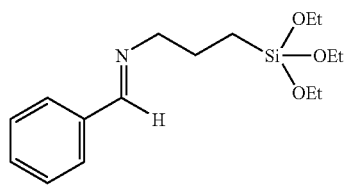

(c) N-benzylidene-3-tris(methoxyethoxyethoxysilyl)-1-propaneamine

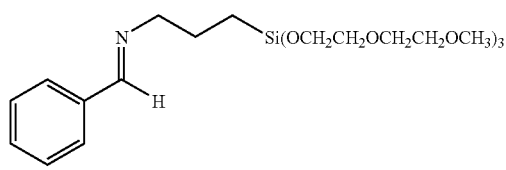

(d) N-pyrrole-3-(triethoxysilyl)-1-propaneamine

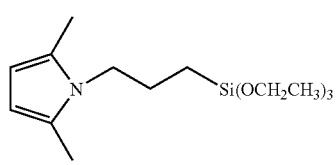

(e) N-pyrrole-3-tris(methoxyethoxyethoxysilyl)-1-propaneamine

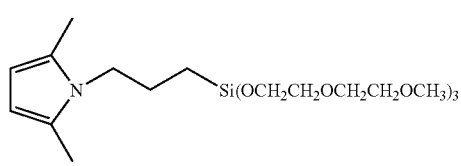

Table 1 provides the Mooney viscosity ($ML_{(1+4)}/100°$ C.), glass transition temperature (Tg), % styrene, and %vinyl for the five polymers.

TABLE 1

Polymer Characterization

| Polymer | Control (a) | Imine-TEOS (b) | Imine-GLYME (c) | Pyrrole-TEOS (d) | Pyrrole-GLYME (e) |
|---|---|---|---|---|---|
| $ML_{(1+4)}/100°$ C. | 40 | 48 | 52 | 45 | 39 |
| Tg (midpt) ° C. | −23.2 | −23.1 | −22.6 | −23.0 | −22.8 |
| % Styrene | 27.2 | 26.0 | 26.3 | 26.9 | 26.9 |
| % Vinyl | 40.0 | 41.2 | 41.7 | 39.8 | 40.5 |

Example 7

A representative example of changes in polymer reactivity to hydrolysis and condensation are provided.

In this example, the prepared polymer was dissolved in hexane at approximate 15 wt % solids and was tested for its zero time molecular weight. Each polymer/hexane solution was then injected into steaming hot water at pH 7.0-7.6 and exposed for 20 minutes, 60 minutes, or 120 minutes. The precipitated polymer crumb was then re-tested for molecular weight. Table 2 shows that the Imine-TEOS (b) polymer is relatively unstable and reactive towards siloxy condensation, as measured by a rapid increase in polymer molecular weight with exposure time to the steam treament. However, the Imine-GLYME (c) polymer is found to be relatively stable to steam treatment. Stability against the steam treatment can provide significant advantage in polymer production, polymer storage, hexane recycle, and emissions.

TABLE 2

Results of Steam Hydrolysis

| Polymer Time @ 95 C. | Control (a) Mn (g/mol) | Imine-TEOS (b) Mn (g/mol) | Imine-GLYME (c) Mn (g/mol) | Pyrrole-TEOS (d) Mn (g/mol) | Pyrrole-GLYME (e) Mn (g/mol) |
|---|---|---|---|---|---|
| 0 min | 184,000 | 220,000 | 197,000 | 199,000 | 191,000 |
| 20 min | 175,000 | 423,000 | 229,000 | 194,000 | 178,000 |
| 60 min | 177,000 | 676,000 | 235,000 | 192,000 | 180,000 |
| 120 min | 174,000 | 812,000 | 261,000 | 195,000 | 177,000 |

Example 8

Representative example showing compound performance and steam stripping stability.

The five polymers (a)-(e) were prepared as described above. The polymers were compounded as follows: The polymers were prepared and tested for performance in a silica compound utilizing 65 phr of Silica, 70 phr of the experimental polymer, and 30 phr of polybutadiene. Compounds were mixed in a 300 cc Brabender mixer in 3 stages, which consisted of two non-productive stages and one productive stage.

| Stage | Ingredient | phr |
|---|---|---|
| NP1 | Tested Polymer | 70 |
| NP1 | Polybutadiene | 30 |
| NP1 | Silica | 65 |
| NP1 | Siloxy Coupling Agent* | 10.4 |
| NP1 | Naphthenic oil | 20 |
| NP1 | ZnO | 3.5 |
| NP1 | Stearic Acid | 2 |

-continued

| Stage | Ingredient | phr |
|---|---|---|
| NP1 | Diamine AO | 2.2 |
| NP1 | Paraffin Wax | 1.5 |
| NP2 | re-mill | |
| PR | Sulfur | 1.7 |
| | Quanidine/sulfonamide | |
| PR | Accelerators | 3.1 |
| PR | Diamine AO | 0.75 |

*50 wt % active absorbed on black

Rotor speed was adjusted to maintain a constant drop temperature for each compound. Performance indicators include: room temperature (RT) rebound (ASTM D1054), tan δ measurements at 40° C., 5% strain and 10 Hz to reflect Rolling Resistance (RR) (ASTM D5992), and Din Abrasion measurements (ASTM D5963) to indicate treadwear. The results are shown in Table 3.

TABLE 3

Lab Results for Rolling Resistance and Treadwear Indicators

| Example | Polymer Description | RT Rebound | RR-Tan δ 5% 40° C. | Treadwear DIN Abrasion | Stripping Stable |
|---|---|---|---|---|---|
| 8a | Control | 40.8 | 0.22 | 140 | yes |
| 8b | Imine-TEOS | 45.4 | 0.14 | 122 | no |
| 8c | Imine-Glyme | 43.6 | 0.18 | 126 | yes |
| 8d | Pyrrole-TEOS | 42.6 | 0.19 | 134 | yes |
| 8e | Pyrrole-Glyme | 39.8 | 0.22 | 138 | yes |
| | Performance direction | High better | Lower better | Lower better | See Example 7 |

Example 8a shows the base line performance for this class of SBR polymer. Example 8b shows the reduction in tan δ, increase in Rebound, and decrease in Din Abrasion with the Imine-TEOS (b) polymer. However, as already described in Example 7, this polymer is less stable to steam stripping making it difficult to process and store. Example 8c shows a performance improvement by the reduction in tan δ, increase in Rebound and, decrease in Din Abrasion with the advantage of stripping stability when an Imine-GLYME (c) polymer is used. Examples 8d-e show that in some instances a balance should be maintained between compound performance and stripping stability. For example, performance improvements can be lost if stripping stability is increased too much.

While the present invention has been illustrated by the description of one or more embodiments thereof, and while the embodiments have been described in detail, they are not intended to restrict or in any way limit the scope of the appended claims to such detail. Additional advantages and modifications will readily appear to those skilled in the art. The invention in its broader aspects is therefore not limited to the specific details, representative methods and illustrative examples shown and described. Accordingly, departures may be made from such details without departing from the scope of the general inventive concept.

What is claimed is:

1. A polymer comprising (a) a repeat unit provided from a conjugated diene monomer and (b) a terminating group provided from a terminating compound of the formula:

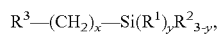

where R³ is

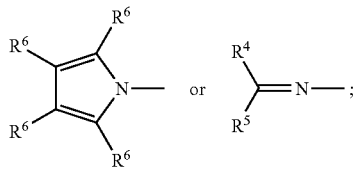

R¹ can be the same or different and is an alkyl, a cycloalkyl, an allyl, and an aryl group with from about 1 to about 18 carbon atoms; R² can be the same or different and is —O (CH₂)$_p$CH₃ or -(A(CH₂)$_n$)$_m$ACH₃ where p is 0, 1, 2, or 3, A is S or O, n is 1, 2, or 3, and m is 1, 2, or 3; x is an integer from about 1 to about 20; y is 0, 1, or 2; R⁶ can be the same or different and is a hydrogen or an alkyl having from about 1 to about 4 carbons.

2. The polymer of claim 1, wherein the polymer is a homopolymer, a copolymer or a terpolymer.

3. The polymer of claim 1, wherein the polymer is a copolymer comprising repeat units of a conjugated diene monomer and a monovinyl aromatic monomer.

4. The polymer of claim 1, wherein the polymer is a copolymer comprising repeat units of 1,3-butadiene and styrene.

5. The polymer of claim 1, wherein the polymer is a terpolymer comprising repeat units of a conjugated diene monomer, a vinyl aromatic hydrocarbon monomer, and a functionalized vinyl aromatic monomer.

6. A rubber composition comprising:
   100 parts by weight of total polymer, where from about 25% to about 100% by weight of the total polymer is a polymer of claim 1; and
   filler in an amount of 10 to 130 phr.

7. The rubber composition of claim 6, wherein the filler is selected from the group consisting of amorphous silica, rubber reinforcing carbon black, a combination of silica and carbon black, and clay.

8. A tire having a component comprising the rubber composition of claim 6.

9. The polymer of claim 1, wherein R³ is

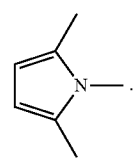

10. The polymer of claim 1, wherein the terminating compound is

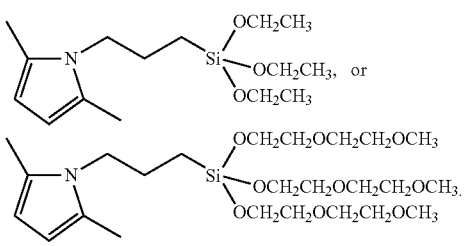

11. A process for making a polymer:
polymerizing monomers comprising conjugated diene monomers by using an initiator to form a polymer with an active terminal end; and
reacting an active terminal end of the polymer with a terminating compound

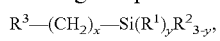

where $R^3$ is

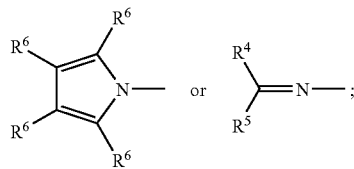

$R^1$ can be the same or different and is an alkyl, a cycloalkyl, an allyl, and an aryl group with from about 1 to about 18 carbon atoms; $R^2$ can be the same or different and is —O(CH$_2$)$_p$CH$_3$ or -(A(CH$_2$)$_n$)$_m$ACH$_3$ where p is 0, 1, 2, or about 3, A is S or O, n is 1, 2, or about 3, and m is 1, 2, or about 3; x is an integer from about 1 to about 20; y is 0, 1, or 2; $R^4$ is an aryl or substituted aryl having from about 6 to about 18 carbon atoms, or a heterocycle or substituted heterocycle having from about 3 to about 18 carbon atoms; $R^5$ is hydrogen or a alkyl group having from about 1 to about 4 carbons; $R^6$ can be the same or different and is a hydrogen or an alkyl having from about 1 to about 4 carbons;
wherein if (i) $R^5$ is H and (ii) $R^4$ is a phenyl or substituted phenyl, then $R^2$ is -(A(CH$_2$)$_n$)$_m$ACH$_3$ and m is 2 or about 3.

12. The process of claim 11, wherein the initiator is an organolithium compound.

13. The process of claim 11, wherein the polymerizing comprises polymerizing a conjugated diene monomer and a monovinyl aromatic monomer to form a copolymer.

14. The process of claim 11, wherein $R^3$ is

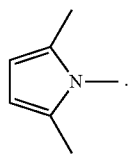

15. The process of claim 11, wherein the terminating compound is

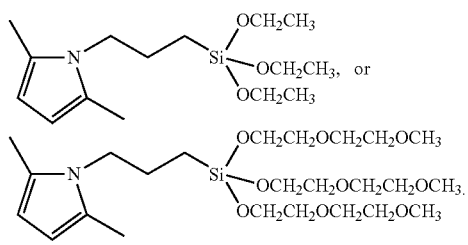

* * * * *

UNITED STATES PATENT AND TRADEMARK OFFICE
CERTIFICATE OF CORRECTION

PATENT NO. : 8,022,159 B2
APPLICATION NO. : 12/276454
DATED : September 20, 2011
INVENTOR(S) : Michael Joseph Rachita et al.

It is certified that error appears in the above-identified patent and that said Letters Patent is hereby corrected as shown below:

In the Specification

Column 7, line 2,

"styrenelbutadiene"     should read     -- styrene/butadiene --

In the Claims

Claim 1, column 14, line 1 through 10,

"where $R^3$ is       should read -- where $R^3$ is

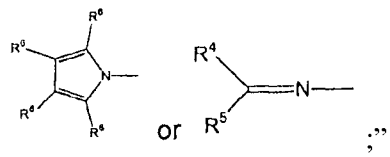   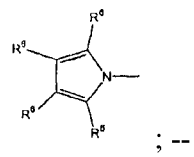

or ;"      ; --

Claim 11, column 15, line 20 through 30,

"where $R^3$ is       should read -- where $R^3$ is

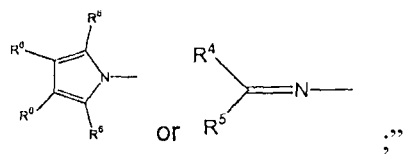   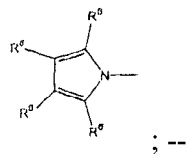

or ;"      ; --

Claim 11, column 15, line 31 through 35,

"$R^2$ can be the same or different and       should read -- $R^2$ can be the same or
is $-O(CH_2)_p CH_3$ or $-(A(CH_2)_n)_m ACH_3$       different and is $-O(CH_2)_p CH_3$ or Signed and Sealed this
Ninth Day of December, 2014

Michelle K. Lee
*Deputy Director of the United States Patent and Trademark Office*

CERTIFICATE OF CORRECTION (continued)
U.S. Pat. No. 8,022,159 B2 where p is 0, 1, 2, or about 3, A is S or O, n is 1, 2, or about 3, and m is 1, 2, or about 3;"

$-(A(CH_2)_n)_m ACH_3$ where p is 0, 1, 2, or 3, A is S or O, n is 1, 2, or 3, and m is 1, 2, or 3; --

Claim 11, column 15, line 36 through column 16, line 7,

"$R^4$ is an aryl or substituted aryl having from about 6 to about 18 carbon atoms, or a heterocycle or substituted heterocycle having from about 3 to about 18 carbon atoms; $R^5$ is hydrogen or a alkyl group having from about 1 to about 4 carbons; $R^6$ can be the same or different and is a hydrogen or an alkyl having from about 1 to about 4 carbons;
wherein if (i) $R^5$ is H and (ii) $R^4$ is a phenyl or substituted phenyl, then $R^2$ is $-(A(CH_2)_n)_m ACH_3$ and m is 2 or about 3."

should read -- $R^6$ can be the same or different and is a hydrogen or an alkyl having from about 1 to about 4 carbons. --